United States Patent [19]

Yamatsu et al.

[11] Patent Number: 4,599,328

[45] Date of Patent: Jul. 8, 1986

[54] THERAPEUTIC AND PREVENTIVE AGENT CONTAINING DOLICHOL

[75] Inventors: Isao Yamatsu; Takeshi Suzuki, both of Ushiku; Shinya Abe, Kukizaki; Kouji Nakamoto, Tsuchiura; Akiharu Kajiwara, Yatabe; Kouichi Katayama, Sakuramura; Hajime Tsunoda; Manabu Murakami, both of Toyosato; Hideki Ono, Sakura; Kouji Yamada, Toride, all of Japan

[73] Assignee: Eisai Co., Ltd., Tokyo, Japan

[21] Appl. No.: 684,871

[22] Filed: Dec. 21, 1984

[30] Foreign Application Priority Data

Dec. 26, 1983 [JP] Japan ............................ 58-244228

[51] Int. Cl.[4] ................. A61K 31/66; A61K 31/035

[52] U.S. Cl. ................................. 514/106; 514/134; 514/739; 514/866

[58] Field of Search .................. 514/739, 134, 106

[56] References Cited

U.S. PATENT DOCUMENTS 4,175,139 11/1979 Kijima et al. .................... 514/739
4,325,974 4/1982 Yamatsu et al. .................. 514/739

Primary Examiner—Frederick E. Waddell
Attorney, Agent, or Firm—Flynn, Thiel, Boutell & Tanis

[57] ABSTRACT

Dolichol or phosphate thereof is useful as a therapeutically treating and preventive agent, in particular, for hyperuricuria, hyperlipemia, diabetes and hepatic diseases.

4 Claims, No Drawings

THERAPEUTIC AND PREVENTIVE AGENT CONTAINING DOLICHOL

The invention relates to a therapeutic treatment and preventive agent containing, as a pharmaceutically effective component, dolichol or a phosphate thereof. The invention agent is effective to treat and prevent, in particular, hyperuricemia, hyperlipemia, arteriosclerosis, diabetes and hepatic diseases; and then improve lipometabolism.

Dolichol is a polyprenol having the following structure and occurs in yeasts and mammals:

(I)

wherein n represents an integer of 14 to 24.

Dolichol is characterized by the presence of two trans-isoprene units and a cis-isoprene unit attached thereto and a saturated alcohol-terminal (α-terminal) isoprene unit. Dolichol is supposed to play an important role in life conservation of organisms and expected to be available as an active ingredient for various pharmaceuticals.

Under these circumstances, we have examined the pharmaceutical availability of dolichol for a long time. As a result of our researches, we have found that dolichol is unexpectedly effective to treat and prevent hyperuricemia such as gout, hyperlipemia, arteriosclerosis, diabetes and hepatic diseases; and then improve lipometabolism.

Dolichol to be used in the embodiments of the present invention may be prepared by any convenient method. That is to say, it may be extracted, for example, from swine liver (cf. F. W. Burgos et al., Biochemical Journal, 88, 470(1963)) or swine pancreas (cf. Japanese Patent Application No. 12622/1983). Alternately, it may be prepared by fermentation with microorganisms. Furthermore it may be chemically synthesized.

The aforementioned chemical structure indicates that dolichol may occur in various forms depending on n. Dolichol being used in the present invention may be either a single compound wherein n is a particular integer (e.g. n is 19) or a mixture of compounds wherein n represents various integers.

For example, dolichol originating from human liver is believed to consist of 0.9% of the compound wherein n is 16; 8.8% of the compound wherein n is 17; 36.6% of the compound wherein n is 18; 37.7% of the compound wherein n is 19; 12.4% of the compound wherein n is 20; 3.2% of the compound wherein n is 21 and 0.7% of the compound wherein n is 22. On the other hand, dolichol originating from swine liver is believed to consist of a small amount of the compound wherein n is 10; 2.5% of the compound wherein n is 16; 19.8% of the compound wherein n is 17; 43.5% of the compound wherein n is 18; 28.6% of the compound wherein n is 19 and 5.5% of the compound wherein n is 20. Furthermore dolichol originating from yeast is believed to consist of 3.0% of the compound wherein n is 12; 14.1% of the compound wherein n is 13; 43.5% of the compound wherein n is 14; 34.5% of the compound wherein n is 15 and 4.8% of the compound wherein n is 16. Dolichol to be used in the embodiments of the present invention may obviously include the dolichols as described above as well as those extracted from other animal and vegetable tissues and having various compositions.

The expression "dolichol phosphate" as used herein means an ester which is formed by bonding the terminal hydroxyl group of dolichol to phosphoric acid and has the following chemical structure;

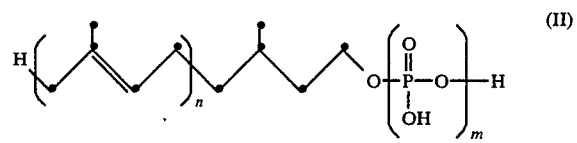
(II)

wherein n represents an integer of 14 to 24 and m represents an integer of 1 to 3.

Similar to free dolichol, dolichol phosphate being used in the present invention may be a single compound wherein n is a particular integer or a mixture of compounds wherein n represents various integers.

The therapeutic effect of the invention will be described below with reference to experimental examples. The effect on hyperuricuria is shown in Experimental Examples 1 and 2; that on hepatic diseases, in No. 3; that on diabetes, in Nos. 4 and 5; and that on hyperlipemia, in Nos. 6 and 7.

EXPERIMENTAL EXAMPLE 1

60 mg/kg of Streptozotocin was injected into the tail vein of each male Sprague-Dawley rat of 140 to 160 g in body weight to thereby induce hyperuricuria experimentally. Three days after the injection of Streptozotocin, 0.3 ml of a 1% dolichol/lecithin emulsion was injected into the femoral muscle of the rat once a day for four days. One day after the final administration, heparinized blood was collected from the aorta under etherization. The heparinized blood was centrifuged at 3,000 r.p.m. for 10 min and then the uric acid in the supernatant was determined. Table 1 shows the result.

TABLE 1

| Group | n | Uric acid |
|---|---|---|
| Normal rats not treated in the way as described in the Experimental Example 1 | 5 | 1.5 ± 0.19 |
| Hyperuricemic rats treated in the way as described in the Experimental Example 1 | 5 | 2.9 ± 0.85* |
| Hyperuricuric rats administered 3 mg of dolichol as described in the Experimental Example 1 | 4 | 1.4 ± 0.22 |

EXPERIMENTAL EXAMPLE 2

50 mg/kg of Streptozotocin was injected into the tail vein of each male Sprague-Dawley rat of 170 to 190 g in body weight to thereby induce hyperuricuria experimentally. 10 days after the injection of Streptozotocin, 0.3 ml of a 1% dolichol monophosphate/lecithin emulsion was injected into the femoral muscle of the rat once a day for 42 days. One day after the final administration, heparinized blood was collected from the aorta under etherization. The heparinized blood was centrifuged at 3,000 r.p.m. for 10 min and then uric acid in the supernatant was determined.

TABLE 2

| Group | n | Uric acid |
|---|---|---|
| Hyperuricemic rats treated in the way as described in the | 8 | 7.3 ± 5.4 |

TABLE 2-continued

| Group | n | Uric acid |
|---|---|---|
| Experimental Example 2 Hyperuricuric rats administered 3 mg of dolichol monophosphate as described in the Experimental Example 2 | 8 | 1.8 ± 0.63* |

The results of the Experimental Examples 1 and 2 clearly indicate that administration of dolichol or its phosphate would significantly lower high uric acid values in blood to a normal level. Accordingly these compounds are extremely effective therapeutic and/or preventive agents for hyperuriemia.

The compounds of the present invention may be administered for treating and/or preventing hyperuricemia such as gout either orally or parenterally, e.g., intramuscularly, hypodermically or intravenously.

EXPERIMENTAL EXAMPLE 3

Effects of dolichol and its phosphate on hepatic regeneration after hepatectomy (1) Method Male Sprague-Dawley rat (7 weeks of age, each 210 to 240 g in body weight) were subjected to hepatectomy according to the method reported by Higgins and Anderson. That is, the rat had an abdominal operation under etherization to remove the right and left median lobes of liver (approximately 72% on average). After suturation, the rat was fed with Oriental Solid Feed and tap water in a usual manner. After a certain period, the rat was exsanguinated under etherization. Then the liver was weighed to calculate the hepatic regeneration rate by the following equation:

$$\frac{\text{Weight of regenerated liver} - \text{Weight of residual liver}}{\text{Weight of removed liver}} \times 100 = \text{Regeneration Ratio (\%)}.$$

wherein the weight of residual liver was determined by subtracting the weight of the removed liver from the weight of the whole liver at the operation which was regarded 4.65 g per 100 g of body weight.

(2) Effects of dolichol on the regeneration rate 30 mg/kg of a dolichol/lecithin emulsion was administered intraperitoneally to a rat once a day for eight consecutive days (five days preoperation and three days post-operation). Table 3 shows the results

TABLE 3

| Group | n | Dose (mg/kg/day) | Regeneration rate (%) |
|---|---|---|---|
| Control group | 14 | — | 40.81 ± 1.97 |
| Dolichol-administered group | 7 | 30 | 48.78 ± 1.54** |

Table 3 indicates that continuous intraperitoneal administration of dolichol of the present invention at a dose of 30 mg/kg/day would significantly raise the regeneration rate.

(3) Effect of dolichol phosphate on the regeneration rate

Three days after the hepatectomy, dolichol monophosphate was intravenously administered to a rat followed by the evaluation after four days, i.e., seven days after the operation. Table 4 shows the result.

TABLE 4

| Group | n | Dose (mg/kg/day) | Regeneration rate (%) | Total protein in blood (mg/dl) |
|---|---|---|---|---|
| Normal rats | 2 | — | — | 6.35 |
| Control | 8 | — | 70.5 ± 2.0 | 5.8 ± 0.05 |
| Dolichol phosphate | 8 | 15 | 77.5 ± 5.2 | 6.1 ± 0.08* |

Table 4 clearly indicates that an intravenous injection of dolichol phosphate after a posthepatectomic increase in blood cholesterol would raise the regeneration rate and significantly increase the total protein content in blood.

The result of this Experimental Example teaches that dolichol and a phosphate thereof according to the invention would accelerate the recovery of the function of hepatic cells at regeneration.

The compounds of the present invention are effective for treating and/or preventing hepatic diseases such as inflammation, denaturation, necrosis, choleresis insufficiency and saccharometabolic disorder caused by alcohol, malnutrition, viruses, chemical substances, toxins or the like.

Thus the compounds of the present invention are effective for treatment and/or preventing hepatic diseases including acute and chronic hepatitis and hepatocirrhosis.

EXPERIMENTAL EXAMPLE 4

60 mg/kg of Streptozotocin was injected into the tail vein of each male Sprague-Dawley rat of 140 to 160 g in body weight to thereby induce diabetes experimentally. Three days after the injection of Streptozotocin, 10 μl of whole blood was collected from the tail vein of the rat to determine the blood sugar content by the glucose oxidase method. The rat showed a blood sugar content of not less than 250 mg/dl, which indicated that it suffered from diabetes. Three days after the injection of Streptozotocin, 0.3 ml of a 1% dolichol/lecithin emulsion was injected into the femoral muscle of the rat four times a day for four days. One month after the final administration, heparinized blood was collected from the aorta under etherization. The heparinized blood was centrifuged at 3,000 r.p.m. for 10 min and the triglycerides and glucose in the supernatant were determined.

Table 5 shows the results.

TABLE 5

| Group | n | Triglyceride (mg/dl) | Glucose (mg/dl) |
|---|---|---|---|
| Normal rats not treated in the way described in the Experimental Example 4 | 5 | 101 ± 6 | 184 ± 10 |
| Diabetic rats treated in the way as described in the Experimental Example 4 | 5 | 765 ± 277 | 548 ± 30 |
| Diabetic rats administered 3 mg of dolichol as described in the Experimental Example 4 | 4 | 199 ± 54 | 477 ± 43 |

EXPERIMENTAL EXAMPLE 5

50 mg/kg of Streptozotocin was injected into the tall vein of each male Sprague-Dawley rat of 170 to 190 g in body weight to thereby induce diabetes experimentally. One day after the injection of Streptozotocin, 10 μl of whole blood was collected from the tail vein of the rat to determine the blood sugar content by the glucose oxidase method. The rat showed a blood sugar content of not less than 250 mg/dl, which indicated that it suffered from diabetes. 10 days after the injection of Streptozotocin, 0.3 ml of a 1% dolichol monophosphate/lecithin emulsion was injected into the femoral muscle of the rat once a day for 42 days. One day after the final administration, heparinized blood was collected from the aorta under etherization. The heparinized blood was centrifuged at 3,000 r.p.m. for 10 min and then triglycerides and glucose in the supernatant were determined.

TABLE 6

| Group | n | Triglyceride (mg/dl) | Glucose (mg/dl) |
|---|---|---|---|
| Diabetic rats treated in the way as described in the Experimental Example 4 | 8 | 2160 ± 1721 | 650 ± 108 |
| Diabetic rats administered 3 mg of dolichol monophosphate as described in the Experimental Example 5 | 8 | 514 ± 361* | 534 ± 64* |

The results in Experimental Examples 4 and 5 clearly indicate that the administration of dolichol or its phosphate, i.e. the compounds of the present invention, significantly lower the content of both triglyceride and glucose.

Accordingly these compounds are extremely effective therapeutic and/or preventive agents for diabetes.

EXPERIMENTAL EXAMPLE 6

60 mg/kg of Streptozotocin was injected into the tail vein of each male Sprague-Dawley rat of 140 to 160 g in body weight to thereby induce hyperlipemia experimentally. Three days after the injection of Streptozotocin, 0.3 ml of a 1% dolichol/lecithin emulsion was injected into the femoral muscle of the rat once a day for four days. One month after the final administration, heparinized blood was collected from the aorta under etherization. The heparinized blood was centrifuged at 3,000 r.p.m. for 10 min and then total protein (TP), albumin (Alb), total cholesterol (T.CHO) and triglycerides (TG) were determined.

Table 7 shows the results.

TABLE 7

| Group | n | TP | Alb (g/dl) | T.CHO (mg/dl) | TG (mg/dl) |
|---|---|---|---|---|---|
| Normal rats not treated in the way as described in the Experimental Example 6 | 5 | 5.9 ± 0.2 | 3.3 ± 0.09 | 66 ± 14 | 101 ± 6 |
| Hyperlipemic rats treated in the way as described in the Experimental Example 6 | 5 | 5.6 ± 0.11* | 2.9 ± 0.22* | 172 ± 26*** | 765 ± 277** |
| Hyperlipemic rats administered 3 mg of dolichol as described in the in the way as described Experimental Example 6 | 4 | 5.6 ± 0.23 | 3.0 ± 0.13 | 89 ± 11### | 199 ± 54### |

EXPERIMENTAL EXAMPLE 7

50 mg/kg of Streptozotocin was injected into the tail vein of each male Sprague-Dawley rat of 170 to 190 g in body weight to thereby induce hyperlipemia experimentally. 10 days after the injection of Streptozotocin, 0.3 ml of a 1% dolichol monophosphate/lecithin emulsion was injected into the femoral muscle of the rat once a day for 42 days. One day after the final administration, heparinized blood was collected from the aorta under etherization. The heparinized blood was centrifuged at 3,000 r.p.m. for 10 min and then total cholesterol (T.CHO), triglycerides (TG), phospholipids (PL) and non-esterified fatty acids (NEFA) in the supernatant were determined.

Table 8 shows the results.

TABLE 8

| Group | n | T.CHO (mg/dl) | TG (mg/dl) | PL (mg/dl) | NEFA (mg/dl) |
|---|---|---|---|---|---|
| Hyperlipemic rats treated in the way as described in the Experimental Example 7 | 8 | 186 ± 49 | 2160 ± 1721 | 415 ± 102 | 2.60 ± 1.1 |
| Hyperlipemic rats administered 3 mg of dolichol monophosphate as described in the Experimental Example 7 | 8 | 82 ± 32*** | 514 ± 361 | 211 ± 78*** | 0.98 ± 0.43** |

The results in Experimental Examples 6 and 7 clearly indicate that administration of dolichol or its phosphate, i.e., the compounds of the present invention, would be effective for treating hyperlipemia. Accordingly these compounds serve as extremely effective lipometabolism improvers and therapeutic and/or preventive agents for arteriosclerosis accompanied with hyperlipemia.

Dolichol and its phosphate which are the compounds of the present invention are highly safe. Therefore it is possible to administer these compounds continuously, which also make the present invention very valuable.

For example, no deaths nor side effects were observed when 1,500 mg/kg of dolichol, i.e., the compound of the present invention was orally administered to SD rats of approximately 200 g in body weight.

The dose depends on the stage of the disease or the age of the patients. These compounds may be administered usually in amounts of approximately 10 to 1,000 mg a day and preferably approximately 50 to 300 mg a day, without particular limitation.

The compounds of the present invention may be formulated in a well-known manner in the art into various forms such as tablets, granules, powders, capsules, injections and suppositories. These compounds may be formulated in a conventional manner by using conventional carriers.

For example, solid pharmaceuticals for oral administration may be prepared by adding an excipient with, if necessary, a binder, a disintegrant, a lubricant, a colorant, a corrigent or the like to the base and then formulating the mixture into a tablet, a coated tablet, granule, powder, capsule or the like in a conventional manner.

Examples of the excipient are lactose, corn starch, white sugar, glucose, sorbitol, crystalline cellulose and silicon dioxide. Examples of the bonder are polyvinyl alcohol, polyvinyl ether, ethylcellulose, methylcellulose, gum arabic, tragacanth, gelatin, shellac, hydroxypropylcellulose, hydroxypropylstarch and polyvinylpyrrolidone. Examples of the disintegrant are starch, agar, gelatin powder, crystalline cellulose, calcium carbonate, sodium hydrogencarbonate, calcium citrate, dextrin and pectin. Examples of the lubricant are magnesium stearate, talc, polyethylene glycol, silica and hardened vegetable oils. Any colorant which is pharmaceutically acceptable may be used. Examples of the corrigent are cacao powder, menthol, aromatic powder, peppermint oil, borneol and cinnamon powder. The obtained tablet or granule may be coated with sugar, gelatin or the like if desired.

An injection may be prepared by adding desired agents such as a pH adjustor, a buffer, a stabilizer and a solubilizing agent to the base and then formulating the mixture into a hypodermic, intramuscular or intravenous injection in a conventional manner.

Processes for preparing dolichol which is the compound of the present invention wil be given for reference.

PREPARATIVE EXAMPLE 1

Preparation of a pancreatic fat extract 1 kg of minced swine pancreas was stirred vigorously in 4 l of acetone to extract oil and fat components. The acetone phase was separated to obtain 4.2 l of a liquor. Then the liquor was concentrated under heating to obtain 500 ml of a concentrate. After cooling the concentrate, a solidified fat phase called a pancreatic fat extract (100 g) was separated.

PREPARATIVE EXAMPLE 2

Preparation of a pancreatic fat extract 2.5 kg of minced swine pancreas was stirred vigorously in 10 l of ethanol to extract oil and fat components. The alcoholic phase was separated to obtain 10.1 l of a liquor. Then the liquor was concentrated under heating to obtain 1.5 l of a concentrate. After cooling the concentrate, a solidified fat phase called a pancreatic fat extract (280 g) was separated.

PREPARATIVE EXAMPLE 3

Preparation of a pancreatic fat extract 200 ml of water, 100 g of swine duodenum (10 g of pancreatin) and 10 ml of a 40% NaOH solution were added to 1 kg of minced swine pancreas. Then the mixture was thoroughly stirred at pH 8.5 and subjected to the activating treatment which was employed in the activation of protease or in preparing pancreatin. Subsequently 4.8 l of acetone was added to the mixture to extract oil and fat components. Then the acetone phase (5.3 ml) was separated.

The precipitate was further defatted and ground to obtain 220 g of pancreatin.

The acetone phase was concentrated under heating to obtain 700 ml of a concentrate. After cooling the concentrate, a solidified fat phase called a pancreatic fat extract (100 g) was separated.

PREPARATIVE EXAMPLE 4

Preparation of a pancreatic fat extract 3 kg of minced swine pancreas was stirred vigorously in 12 l of a 30% ethanol solution (pH 3.0). Then the alcohol/aqueous phase (13 l) was concentrated under heating to obtain 5 l of a concentrate. After cooling the concentrate, 250 g of a solidified pancreatic extract was obtained.

In addition, an intense insulin activity was observed when the liquid phase was administered intraperitoneally to a rat to examine its effect of lowering blood sugar.

PREPARATIVE EXAMPLE 5

1.5 kg of the pancreatic fat extract prepared in the Preparative Example 1 was dissolved in 3 l of methanol. Then 1.7 kg of a 15% aqueous solution of caustic soda was added dropwise to the solution at room temperature under stirring. The mixture was saponified for one hour at 60° to 70° C. and then cooled to 50° C. Susequently the mixture was extracted with 3 l of hexane. The organic phase was washed with 1 l of a solvent mixture (methanol/water 2:1) and allowed to stand at 4° C. overnight. Precipitated crystals were filtered and the filtrate was concentrated. Then the obtained concentrate was purified with silica gel column chromatography by using n-hexane/benzene as an eluent. Consequently 85 mg of dolichol in the form of a colorless oil was obtained. The dolichol prepared in the present Example was identified since the retention time thereof in HPLC coincided with that of a commercial dolichol (Sigma Co., INC. D-4511).

HPLC:
stationary phase: nucleosil $C_{18}$ $7\mu \times 25$ cm,
mobile phase: a solvent mixture consisting of 520 parts of isopropyl alcohol, 240 parts of methanol, 40 parts of n-hexane and 18 parts of water,
flow rate: 1 ml/min,
detection wavelength: 210 nm.

Now a Formulation Example in which dolichol which is the compound of the present invention and referred to as the base in the Example is used as an active ingredient will be given.

FORMULATION EXAMPLE

Tablets base: 10 g
silicic anhydride: 50 g
crystalline cellulose: 70 g
corn starch: 36 g
hydroxypropylcellulose: 10 g
magnesium stearate: 4 g The mixture was formulated into tablets each weighing 180 mg in a conventional manner.

The embodiments of the invention in which an exclusive property or privilege is claimed are defined as follows:

1. A method of treating diabetes which comprises administering to a diabetic subject requiring such treatment, a therapeutically effective amount of a diabetes treating composition comprising a pharmaceutical carrier and an effective amount of at least one dolichol substance selected from the group consisting of compounds having the formulas and wherein n is an integer of 14 to 24, and m is an integer of 1 to 3.

2. A method as claimed in claim 1, in which said substance has the formula

3. A method as claimed in claim 1, in which said substance has the formula

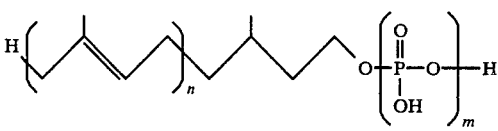

4. A method as claimed in claim 1, in which the amount of said substance administered is from 10 to 1000 mg/day.

* * * * *